United States Patent
Effland et al.

Patent Number: 5,179,099
Date of Patent: Jan. 12, 1993

[54] 2,3-DIHYDRO-1-(PYRIDINYLAMINO)-INDOLES

[75] Inventors: Richard C. Effland, Bridgewater; David G. Wettlaufer, Phillipsburg; Joseph T. Klein, Bridgewater, all of N.J.

[73] Assignee: Hoechst-Roussel Pharmaceuticals Incorporated, Somerville, N.J.

[21] Appl. No.: 705,220

[22] Filed: May 24, 1991

Related U.S. Application Data

[63] Continuation-in-part of Ser. No. 388,415, Aug. 2, 1989, abandoned.

[51] Int. Cl.$^5$ .................. C07D 401/12; A61K 31/44
[52] U.S. Cl. .................... 514/278; 514/339; 546/15; 546/273
[58] Field of Search .............. 546/269, 15, 17; 514/339, 278

[56] References Cited

U.S. PATENT DOCUMENTS

| | | | |
|---|---|---|---|
| 4,345,081 | 8/1982 | Ong et al. | 546/17 |
| 4,868,190 | 9/1989 | Effland et al. | 514/337 |

FOREIGN PATENT DOCUMENTS 0287982A 10/1988 European Pat. Off. .

Primary Examiner—Jane T. Fan
Attorney, Agent, or Firm—Elliott Korsen

[57] ABSTRACT

This invention relates to 2,3-dihydro-1-(pyridinylamino)-indoles of the formula

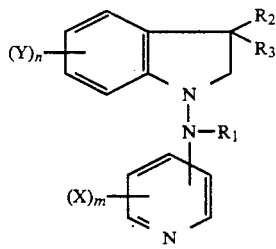

wherein $R_1$ is hydrogen, loweralkyl, aryl, arylloweralkyl, alkenyl, alkynyl or heteroarylloweralkyl selected from the group consisting of pyridinylmethyl, pyridinylethyl, thienylmethyl, thienylethyl; $R_2$ and $R_3$ and independently hydrogen, loweralkyl, aryl, arylloweralkyl or heteroarylloweralkyl selected from the group consisting of pyridinylmethyl, pyridinylethyl, thienylmethyl, thienylethyl; or $R_2$ and $R_3$ together form a cycloalkane ring of 4 to 6 carbons or a spiro-fused aryl or heteroaryl; the term heteroaryl signifying a group selected from pyridine or thiophene; X and Y are independently hydrogen, halogen, hydroxy, loweralkyl, loweralkoxy, nitro, amino or trifluoromethyl; m and n are independently integers of 1 to 3, or a pharmaceutically acceptable acid addition salt thereof or where appropriate, an optical, geometrical or stereoisomer or racemic mixture thereof. The compounds of this invention are useful as analgesics, anticonvulsants, and for the treatment of memory dysfunctions characterized by a cholinergic deficit.

3 Claims, No Drawings

2,3-DIHYDRO-1-(PYRIDINYLAMINO)-INDOLES

This application is a continuation-in-part of pending U.S. patent application Ser. No. 388,415 filed Aug. 2, 1989, now abandoned.

This invention relates to compounds of the formula

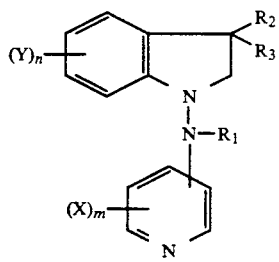

wherein $R_1$ is hydrogen, loweralkyl, aryl, arylloweralkyl, alkenyl, alkynyl or heteroarylloweralkyl selected from the group consisting of pyridinylmethyl, pyridinylethyl, thienylmethyl, thienylethyl; $R_2$ and $R_3$ are independently hydrogen, loweralkyl, aryl, arylloweralkyl or heteroarylloweralkyl selected from the group consisting of pyridinylmethyl, pyridinylethyl, thienylmethyl, thienylethyl; or $R_2$ and $R_3$ together form a cycloalkane ring of 4 to 6 carbons or a spiro-fused aryl or heteroaryl; the term heteroaryl signifying a group selected from pyridine or thiophene; X and Y are independently hydrogen, halogen, hydroxy, loweralkyl, loweralkoxy, nitro, amino trifluoromethyl; m and n are independently integers of 1 to 3, or a pharmaceutically acceptable acid addition salt thereof or, where appropriate, an optical, geometrical or stereoisomer or racemic mixture thereof.

Preferred embodiments of the invention are those of Compound I where $R_1$ is selected from hydrogen and loweralkyl, $R_2$ is selected from hydrogen and loweralkyl, and $R_3$ is selected from hydrogen and loweralkyl.

Most preferred embodiments of the invention are those of Compound I where $R_1$ is selected from loweralkyl and $R_2$ and $R_3$ are selected from hydrogen.

Throughout the specification and the appended claims, a given chemical formula or name shall encompass all optical and stereoisomers thereof and racemic mixtures where such isomers and mixtures exist.

In the above definition, the term "lower" means the group it is describing contains from 1 to 6 carbon atoms. The term "alkyl" refers to a straight or branched chain hydrocarbon containing no unsaturation, e.g., methyl, ethyl, isopropyl, t-butyl, neopentyl, n-hexyl, etc.; the term "arylloweralkyl" refers to a monovalent substituent which consists of an "aryl" group e.g., phenyl, o-tolyl, m-methoxyphenyl, heteroaryl, pyridyl, thiophene, etc., as defined by the formula

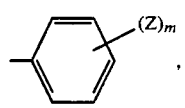

where Z is as defined below, and m is an integer of 1 to 3, linked through a loweralkylene group having its free valence bond from a carbon of the loweralkylene group, and having a formula of

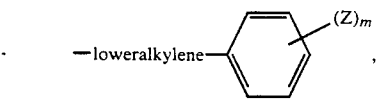

where Z is hydrogen, halogen, loweralkyl, loweralkoxy, $CF_3$, $NO_2$, $NH_2$ or OH and m is as previously defined; the term "alkylene" refers to a bivalent radical of the lower branched or unbranched alkyl group it is derived from having valence bonds from two terminal carbons thereof; e.g., methylene (—$CH_2$—), ethylene (—$CH_2CH_2$—), propylene (—$CH_2CH_2CH_2$—), isopropylene

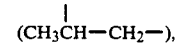

etc,; the term "heteroaryl" refers to an aromatic heterocyclic radical selected from pyridyl or thiophene; and the term "heteroarylloweralkyl" refers to a loweralkyl group having a heteroaryl substituent thereon; the term "alkoxy" refers to a monovalent substituent which consists of an alkyl group linked through an ether oxygen having its free valence bond from the ether oxygen, e.g., methoxy, ethoxy, propoxy, butoxy, pentoxy, etc.; and the term "halogen" refers to a member of the halogen family consisting of fluorine, chlorine, bromine and iodine.

The compounds of the present invention are prepared in the following manner. The substituents are as defined above unless indicated otherwise.

Compound I of the invention is prepared through the reduction of 1,3-dihydro-1-(4-pyridinylamino)-2H-indol-2-one, of the formula:

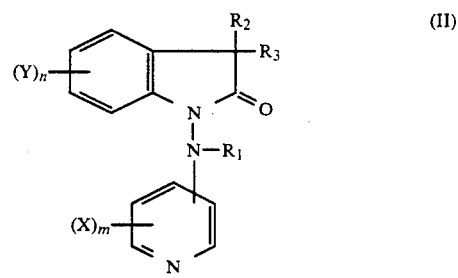

This reduction is typically carried out in the presence of a reducing agent, e.g., a borane-tetrahydrofuran complex, lithium aluminum hydride, etc., in the presence of an ethereal solvent, e.g., tetrahydrofuran, and an inert atmosphere, e.g., nitrogen, etc., at a temperature of 0° to 25° C. to reflux for ¼ to 3 hours. Compound II is prepared by reacting Compound III, a 1-aminooxindole of the formula

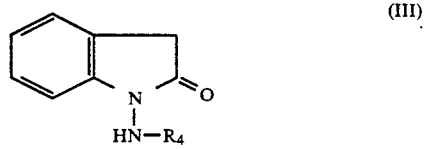

where $R_4$ is hydrogen or loweralkyl, with halopyridine hydrochloride. This reaction is typically conducted with compound III in solution with a loweralkanol or phenolic solvent, i.e., phenol, isopropanol, butanol, etc., at a temperature of 80° C. to 150° C. for ½ to 24 hours. Compound III is typically synthesized utilizing procedures described in Baumgarten et al., *J. Am. Chem. Soc.* 82, 3977–82 (1960), which describes the formation of 1-aminooxindole by the reduction of 3-cinnolinol with zinc and $H_2SO_4$ and by thermal cyclization of O-hydrazinophenylacetic acid.

Compounds of the present invention are useful as analgesic agents due to their ability to alleviate pain in mammals. The activity of the compounds is demonstrated in the phenyl-para-quinone writhing assay in mice, a standard assay for analgesia [*Proc. Soc. Exptl. Biol. Med.*, 95,729 (1957)]. Presented in Table 1 is the analgesic effect of some of the compounds of the invention expressed either as the subcutaneous dose at which 50% of the phenyl-para-quinone induced writhing is inhibited in the animals, i.e., the $ED_{50}$ value, or, as the % decrease in writhing at a given dose.

TABLE 1

| Compound | $ED_{50}$ or % Inhibition of Writhing (s.c.) |
| --- | --- |
| 2,3-Dihydro-N-(4-pyridinyl)-1H-indol-1-amine | 74% at 20 mg/kg |
| 2,3-Dihydro-N-propyl-N-(4-pyridinyl)-1H-indol-1-amine oxalate | 100% at 20 mg/kg |
| Aspirin (standard) | $ED_{50}$ = 32.8 mg/kg |

The analgesic relief of pain is achieved when the compounds of the invention are administered to a subject requiring such treatment at an effective oral, parenteral or intravenous dose of from 0.01 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regiments should be adjusted according to the individual need and the professional judgement of the person administering or supervising the administration of the compound. It is further to be understood that the dosages set forth herein are examples only and that they do not, to any extent, limit the scope or practice of the invention.

The compounds of the present invention are also useful in the treatment of various memory dysfunctions characterized by decreased cholinergic function such as that found in Alzheimer's Disease.

This utility is demonstrated in the Dark Avoidance Assay.

Dark Avoidance Assay

In this assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chambers, the animal re-enters the dark compartment shortly after being placed in the test chamber 24 hours later. The effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. The activity of some of the compounds of the instant invention in the assay are given below in Table 2.

TABLE 2

| Compound | Dose (mg/kg of body wt) | % of Animals With Scopolamine Induced Memory Deficit Reversal |
| --- | --- | --- |
| 2,3-Dihydro-N-(4-pyridinyl)-1H-indol-1-amine | 0.3 mg/kg s.c. | 53% |
| Tacrine (standard) | 0.63 mg/kg s.c. | 13% |
| Pilocarpine (standard) | 1.25 mg/kg s.c. | 19% |

The compounds of the invention are also useful as anticonvulsants due to their anticonvulsant activity in mammals. Anticonvulsant activity is measured in the male mouse using the supramaximal electroshock (SES) assay described in *Arch. Int.* Pharmacodyn. 92:97–107, 1952. In this procedure, groups of male mice are used. Drugs are prepared using distilled water and, if insoluble, a surfactant is added. Control animals receive vehicle. Drugs are routinely administered interperitoneally (i.p.). The dosage volume is 10 ml/kg. A primary screen is given a 30 minute pretreat. The animals' eyes are placed across the output terminals of an A.C. shocker that delivers 206 volts rms for 300 msec. Electrode paste coats the animals' eyes at the point of contact with the terminals. A compound is considered to give protection if the mouse does not exhibit extensor tonus. Protection is expressed as normalized percent inhibition relative to vehicle control.

The anticonvulsant activity of some of the compounds is given below in Table 3.

TABLE 3

| Compound | % Inhibition |
| --- | --- |
| 2,3-Dihydro-N-(4-pyridinyl)-1H-indol-1-amine | −40% at 15 mg/kg i.p. |
| 2,3-Dihydro-N-propyl-N-(4-pyridinyl)-1H-indol-1-amine oxalate | −40% at 10 mg/kg i.p. |
| Phenobarbital (standard) | −50% at 8.4 mg/kg i.p. |

Effective amounts of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ®, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
2,3-Dihydro-N-(3-nitro-4-pyridinyl)-1H-indol-1-amine;
2,3-Dihydro-3-methyl-N-propyl-N-(4-pyridinyl)-1-H-indol-1-amine;
N-Ethyl-2,3-dihydro-3,3-dimethyl-N-(3-methyl-4-pyridinyl)-1H-indol-1-amine;
N-Butyl-N-(3-fluoro-4-pyridinyl)-2,3-dihydro-5-methyl-3-phenylmethyl-1H-indol-1-amine;
N-(3-Amino-4-pyridinyl)-3,3-diethyl-2,3-dihydro-1H-indol-1-amine;
2,3-Dihydro-N-propyl-N-(3-propyl-4-pyridinyl)-1H-indol-1-amine;
2,3-Dihydro-6-methyl-N-(3-nitro-4-pyridinyl)-N-(2-propenyl)-1H-indol-1-amine;
2,3-Dihydro-N-methyl-N-(3-methyl-4-pyridinyl)-3-phenylmethyl-1H-indol-1-amine;
2,3-Dihydro-N-(2-propynyl)-N-(4-pyridinyl)-1H-indol-1-amine;
N-(3-Amino-4-pyridinyl)-3,3-diethyl-2,3-dihydro-N-propyl-1H-indol-1-amine;
N-(3-Fluoro-4-pyridinyl)-2,3-dihydro-3-methyl-1H-indol-1-amine;
N-(3-Amino-4-pyridinyl)-N-butyl-2,3-dihydro-3-phenylethyl-1H-indol-1-amine;
2,3-Dihydro-N-(4-nitro-3-pyridinyl)-1H-indol-1-amine;
N-(4-Fluoro-3-pyridinyl)-2,3-dihydro-3-methyl-1H-indol-1-amine;
2,3-Dihydro-N-propyl-N-(3-pyridinyl)-1H-indol-1-amine;
1,2',3,3'-Tetrahydro-N-(4-pyridinyl)-spiro[2H-indene-2,3'-[3H]indol]-1'-amine The following examples are for illustrative purposes only and are not to be construed as limiting the invention. All temperatures are given in degrees centigrade (°C.) unless otherwise designated.

EXAMPLE 1

2,3-Dihydro-N-(4-pyridinyl)-1H-indol-1-amine

To a stirred solution consisting of 1,3-dihydro-1-(4-pyridinylamino)-2H-indol-2-one (5.00 g) and THF (500 ml) was added borane-THF complex (66.7 ml, 1M concentration). The flask was fitted with reflux condensor and nitrogen inlet. The reaction mixture was heated at reflux 45 minutes followed by cooling to room temperature and concentrated. To the resulting foam was slowly added 5% aqueous hydrochloric acid (500 ml) and methanol (500 ml) after which time the reaction mixture was heated at reflux for 3 hours. The solution was cooled to room temperature and neutralized with saturated aqueous sodium bicarbonate. After gas evolution had ceased, the aqueous layer was extracted four times with ethyl acetate and once with ether. The combined organic layers were washed with water, brine, and dried ($K_2CO_3$). Filtration and concentration gave the crude product.

Purification via preparative high performance liquid chromatography (HPLC) afforded 2.20 g (47%) of 2,3-dihydro-N-(4-pyridinyl)-1H-indol-1-amine, a solid, m.p. 125°–126.5° C.

| ANALYSIS: | | | |
|---|---|---|---|
| Calculated for $C_{13}H_{13}N_3$: | 73.91% C | 6.20% H | 19.89% N |
| Found: | 73.60% C | 6.23% H | 20.01% N |

EXAMPLE 2

2,3-Dihydro-N-propyl-N-(4-pyridinyl)-1H-indol-1-amine oxalate

To a solution consisting of 2,3-dihydro-N-(4-pyridinyl)-1H-indol-1-amine (2.20 g) and DMF (95 ml), cooled to 0° C. under nitrogen, was added sodium hydride (0.27 g). Stirring was continued at 0° C. for 50 minutes at which time bromopropane (1.05 ml) was added dropwise. After 2 hours, the reaction mixture was poured into water and ethyl acetate. The layers were separated and the aqueous layer extracted twice with ethyl acetate and once with ether. The combined organic layers were washed with brine and dried ($K_2CO_3$). Filtration and concentration gave the crude product.

Purification via flash column chromatography afforded 1.80 g (68%) of 2,3-dihydro-N-propyl-N-(4-pyridinyl)-1H-indol-1-amine as a foam. The oxalate was prepared with 0.97 eq. oxalic acids in absolute ethanol and ether. The resulting solid was washed with ether, m.p. 165.5°–166.5° C.

| ANALYSIS: | | | |
|---|---|---|---|
| Calculated for $C_{18}H_{21}N_3O_4$: | 62.96% C | 6.16% H | 12.24% N |
| Found: | 62.92% C | 6.10% H | 12.21% N |

EXAMPLE 3

2,3-Dihydro-N-(3-fluoro-4-pyridinyl)-N-propyl 1H-indol-1-amine maleate

To a stirred solution consisting of 2,3-dihydro-N-(3-fluoro-4-pyridinyl)-1H-indol-1-amine (5.00 g) and DMF (198 ml) cooled to 0° under nitrogen was added sodium hydride (0.57 g). The resulting mixture was stirred at 0° C. for 30 minutes and bromopropane (2.1 ml) was added. The ice bath was removed and the flask warmed to room temperature. Stirring was continued for 1.5–2 hours, until complete reaction was observed by thin layer chromatography. The mixture was poured into water and extracted with ethyl acetate (4–5 times). The combined organic layers were washed with water (7–8 times), brine, and dried ($K_2CO_3$). Filtration, concentration, and purification by flash column chromatography (silica gel, 50% ether/hexanes) afforded 2.90 g of the desired product as an oil. The maleate was prepared in abs. ethanol with 1 eq. maleic acid. A highly crystalline solid was recovered, m.p. 133.5°–135.5° C.

| Analysis: | | | |
|---|---|---|---|
| Calculated for: | 62.01% C | 5.72% H | 10.85% N |
| Found: | 61.89% C | 5.67% H | 10.68% N |

EXAMPLE 4

2,3-Dihydro-N-(3-fluoro-4-pyridinyl)-1H-indol-1-amine

To a stirred solution consisting of 1,3-dihydro-1-(3-fluoro-4-pyridinylamino)-2H-indol-2-one (2.00 g) and tetrahydrofuran (121 ml) cooled to 0° C. under nitrogen was added borane-tetrahydrofuran complex (32.9 ml) over 5–7 minutes. The reaction mixture was stirred an additional 5 minutes at 0° C. and allowed to warm to room temperature by removal of the ice bath. Stirring was continued at room temperature for 4–6 hours, until the reaction was complete by TLC. The reaction mixture was placed in the refrigerator overnight.

To the reaction mixture was slowly added 5% aq. HCl (100 ml) and methanol (100 ml). This flask was warmed at reflux 20–30 minutes. The reaction mixture was concentrated by 40–50% volume and aq. sodium bicarbonate added to make basic. The reaction mixture was extracted with ethyl acetate (3×) and ether (1×), washed, dried, ($K_2CO_3$), filtered and concentrated to give the crude product.

The above reaction was repeated twice (2×6.00 g) in THF (2×363 ml) with borane-tetrahydrofuran complex (2×98.8 ml). The reaction mixtures were hydrolyzed with 5% aq. HCl (2×280 ml) and methanol (2×280 ml) for 20–30 minutes. The product was isolated by basifying and extraction with ethyl acetate and ether.

All of the above crude product was combined and purified via preparative HPLC (silica gel, 2% triethylamine/ethyl acetate). Recrystallization from ethyl acetate afforded 5.0 g of a solid which was nearly pure. The above solid was again recrystallized from ethyl acetate affording 3.00 g as a solid, mp: 155°–157° C.

| Analysis: | | | |
|---|---|---|---|
| Calculated for: | 68.11% C | 5.28% H | 18.33% N |
| Found: | 68.02% C | 5.24% H | 18.23% N |

We claim:

1. A 2,3-dihydro-1-(pyridinylamino)indole of the formula

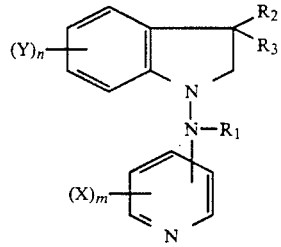

wherein $R_1$ is hydrogen, loweralkyl, aryl, arylloweralkyl, loweralkenyl or loweralkynyl; $R_2$ and $R_3$ together form a spiro-fused cycloalkane ring of 4 to 6 carbons; X and Y are independently hydrogen, halogen, hydroxy, loweralkoxy, nitro, amino or trifluoromethyl; aryl is phenyl, unsubstituted or substituted with halogen, lower alkyl, lower alkoxy $CF_3$, $NO_2$, $NH_2$ or OH; m and n are independently integers of 1 to 3, or a pharmaceutically acceptable acid addition salt thereof, or, where applicable, an optical, geometrical or stereoisomer or racemic mixture thereof.

2. An analgetic pharmaceutical composition which comprises an effective pain alleviating amount of a compound as defined in claim 1 and a suitable carrier therefor.

3. A method of alleviating pain in a mammal which comprises administering to such a mammal a pain alleviating effective amount of a compound as defined in claim 1.

* * * * *